United States Patent [19]
Hennessy et al.

[11] Patent Number: 5,888,994
[45] Date of Patent: Mar. 30, 1999

[54] FLUORINATED VITAMIN $D_3$ ANALOGS

[75] Inventors: Bernard Michael Hennessy, Nutley; Milan Radoje Uskokovic, Upper Montclair, both of N.J.

[73] Assignee: Hoffmann-La Roche Inc., Nutley, N.J.

[21] Appl. No.: 857,883

[22] Filed: May 16, 1997

Related U.S. Application Data

[60] Provisional application No. 60/018,187 May 23, 1996.

[51] Int. Cl.$^6$ .......................... A61K 31/59; C07C 401/00
[52] U.S. Cl. ............................................. 514/167; 552/653
[58] Field of Search ............................. 552/653; 514/167

[56] References Cited

U.S. PATENT DOCUMENTS

| | | |
|---|---|---|
| 4,804,502 | 2/1989 | Baggiolini et al. . |
| 5,039,671 | 8/1991 | Baggiolini et al. . |
| 5,145,846 | 9/1992 | Baggiolini et al. ...................... 514/167 |
| 5,200,536 | 4/1993 | Ikekawa et al. . |
| 5,206,230 | 4/1993 | Ikekawa et al. . |
| 5,210,237 | 5/1993 | Kobayashi et al. . |
| 5,428,029 | 6/1995 | Doran et al. ............................ 514/167 |
| 5,451,574 | 9/1995 | Baggiolini et al. . |
| 5,512,554 | 4/1996 | Baggiolini et al. . |

FOREIGN PATENT DOCUMENTS

| | | |
|---|---|---|
| 38635/93 | 11/1993 | Australia . |
| 13644/95 | 9/1995 | Australia . |
| 0599114 | 6/1994 | European Pat. Off. . |
| 0 808 831 | 11/1997 | European Pat. Off. . |
| WO 91/15475 | 10/1991 | WIPO . |
| WO 92/03414 | 3/1992 | WIPO . |
| WO 93/19044 | 9/1993 | WIPO . |

OTHER PUBLICATIONS

J. Steroid Biochem. Mol. Biol. (Feb. 1996), 57 (3/4), 197–202, Chem. Abs. of; Zhao et al.

Doran, et al. Characterization of Human Cells In Vitro, J. Invest. Dermatol. 96: 34–8 (1991).

*Primary Examiner*—Deborah C. Lambkin
*Attorney, Agent, or Firm*—George W. Johnston; Patricia S. Rocha-Tramaloni; Robert A. Silverman

[57] ABSTRACT

A compound of formula I

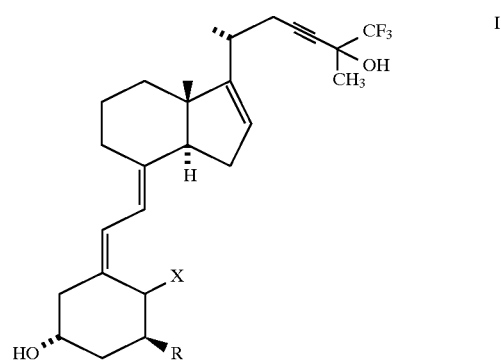

wherein R is hydrogen, fluorine or hydroxy, and X is $=CH_2$ or when R is hydroxy, X is hydrogen or $=CH_2$ which are useful in the treatment of hyperproliferative disorders, neoplastic diseases and sebaceous gland diseases.

8 Claims, No Drawings

FLUORINATED VITAMIN D₃ ANALOGS

This is a provisional application Ser. No. 60/018,167 filed May 23, 1996.

BACKGROUND OF THE INVENTION

The invention relates to Vitamin $D_3$ analogs, particularly 16-ene-23-yne-trifluoro analogs of Vitamin $D_3$.

SUMMARY OF THE INVENTION

The invention relates to a compound of the formula

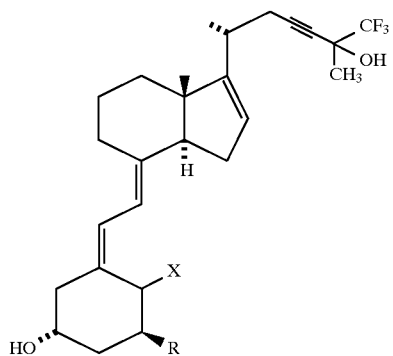

wherein R is hydrogen, fluorine or hydroxy, and X is $=CH_2$ or when R is hydroxy, X is hydrogen or $=CH_2$.

The compounds of formula I induce differentiation and inhibition of proliferation in various skin and cancer cell lines. Accordingly, the compounds of formula I are useful as agents for the treatment of hyperproliferative skin diseases, such as, psoriasis. Compounds of formula I are also useful in the treatment of neoplastic diseases, such as, leukemia and sebaceous gland diseases, such as, acne or sebhorrheic dermatitis.

DETAILED DESCRIPTION OF THE INVENTION

In the formulas presented herein, the various substituents are illustrated as joined to the nucleus by one of the following notations: a wedged solid line (━) indicating a substituent which is above the plane of the molecule, (β-orientation); a wedged dotted line (⋯⋯) indicating a substituent which is below the plane of the molecule (α-orientation); or a wavy line (∼) indicating a substituent either above or below the plane of the molecule.

The compounds of formula I induce differentiation and inhibition of proliferation in various skin and cancer cell lines. Accordingly, the compounds of formula I are useful as agents for the treatment of hyperproliferative skin diseases, such as, psoriasis. Compounds of formula I are also useful in the treatment of neoplastic diseases, such as, leukemia and sebaceous gland diseases, such as, acne or seborrheic dermatitis.

The invention also relates to a pharmaceutical composition comprising a compound of formula I and a method of treating the above mentioned disease states by administration of the compound of formula I.

In a preferred embodiment, R is hydroxy.

An embodiment of the invention is a mixture comprising epimers of the formula

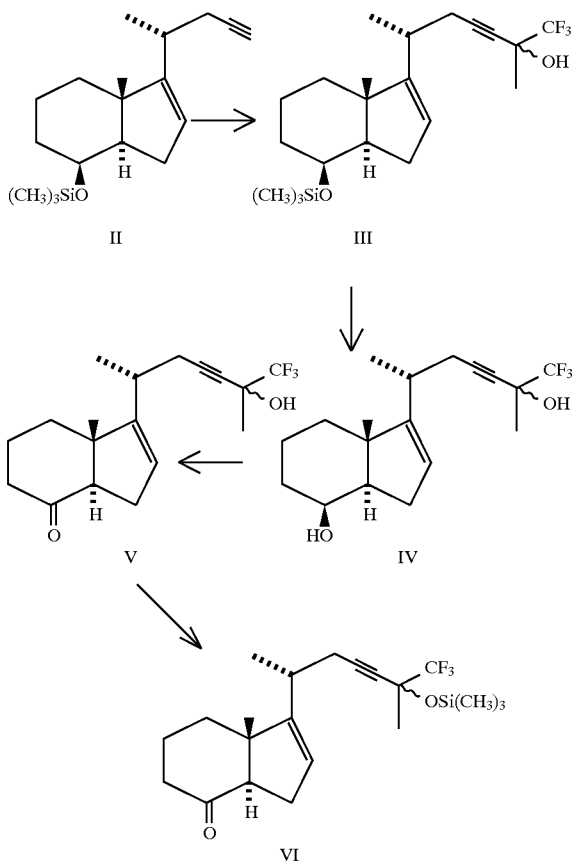

wherein R and X are as described above.

The compounds of formula I are prepared as hereafter described in Schemes I–II and the Examples.

In the above Scheme I, the compound of formula II, [3aS,[3(S*), 3aα,7α,7aβ]]-[[3a,4,5,6,7,7a-hexahydro-3α-methyl-3-(1-methyl-3-butynyl)-1H-inden-7-yl]oxy]-trimethylsilane, a known compound, is converted to a compound of formula III, by reaction with n-butyl-lithium and trifluoroacetone in a ether solvent such as tetrahydrofuran. The reaction is carried out at −100° C. to 0° C., preferably −78° C.

The compound of formula III is converted to the compound of formula IV by reaction with tetrabutyl-ammonium fluoride in a ether solvent, such as tetrahydrofuran. The reaction is carried out at 0°–50° C., preferably room temperature, preferably under an argon atmosphere.

The compound of formula IV is converted to the compound of formula V by reaction with pyridinium dichromate and pyridinium p-toluene sulfonate in a chloronated hydrogen solvent such as methylene chloride.

The compound of formula V is converted to the compound of formula VI by reaction with trimethylsilyl-imidazole in a chlorinated solvent such as methylene chloride. Preferably, the reaction is carried out under an argon atmosphere.

Z)-3,5-bis[[1,1 dimethylethyl)dimethylsilyl]oxy] cyclohexylidene]ethyl]diphenylphosphine oxide in tetrahydrofuran, preferably under argon, followed by removal of the protecting silyl groups.

Alternatively, the compound of formula VI is converted to the compound of formula Id by reaction with [3S-(3α,5β,Z)-2-[2-methylene-3-fluoro-5-[[(1,1 dimethylethyl) dimethyl-silyl]oxy] cyclohexylidene]ethyl]diphenyl phos-

SCHEME II

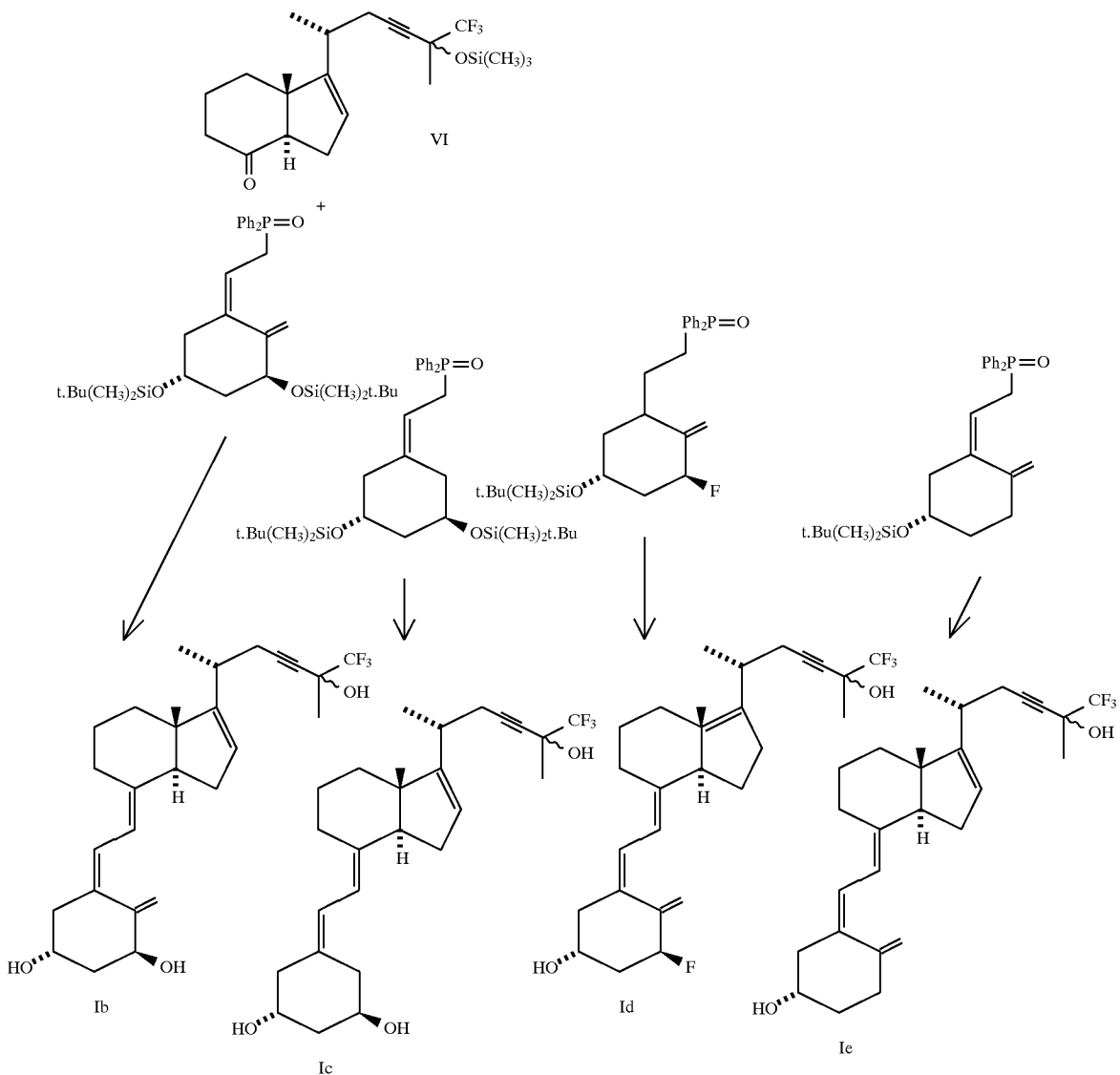

In the above Scheme II, the compound of formula VI is converted to the compound of formula Ib by reaction with [3S-(1Z,3α,5β)]-[2-[3,5-bis[[1,1-dimethylethyl) dimethylsilyl]oxy]-2-methylenecyclohexylidene]ethyl] diphenylphosphine oxide in tetrahydrofuran, preferably under argon in the presence of n-butyl lithium as a base. This reaction is followed by removal of the protecting silyl groups using tetrabutylammonium fluoride in tetrahydrofuran as a solvent.

Alternatively, the compound of formula VI is converted to the compound of formula Ic by reaction with [3R-(3α,5β, phine oxide in tetrahydrofuran, preferably under argon, followed by removal of the protecting silyl groups.

Alternatively, the compound of formula VI is converted to the compound of formula Ie by reaction with [5S,Z)-2-[2-[2-methylene-5-[[(1,1-dimethylethyl)dimethylsilyl] oxy] cyclo-hexylidene]ethyl] diphenyl phosphine oxide in tetrahydrofuran, preferably under argon, followed by removal of the protecting silyl groups.

Any conventional separation method known to those skilled in the art can be used at any point in the preparation of a compound of formula I to separate the epimeric mixture to either the (R) or (S) epimer.

The compound of formula I can be administered orally, for example, in the form of tablets, coated tablets, dragees, hard or soft gelatin capsules, solutions, emulsions or suspensions. The administration can, however, also be effected rectally, for example, in the form of suppositories or parenterally, for example, in the form of injection solutions.

A composition in accordance with the invention can be processed with pharmaceutically inert, inorganic or organic excipients for the manufacture of tablets, coated tablets, dragees and hard gelatin capsules. Lactose, corn starch or derivatives thereof, talc, stearic acid or its salts, and the like, can be used as such excipients, for example, for tablets, dragees and hard gelatin capsules.

Suitable excipients for soft gelatin capsules are, for example, vegetable oils, waxes, fats, semi-solid and liquid polyols, and the like; depending on the nature of the active ingredient. No excipients are, however, usually required in the case of soft gelatin capsules.

Suitable excipients for the preparation of solutions and syrups, are, for example, water, polyols, saccharose, invert sugar, glucose and the like.

Suitable excipients for injection solutions are, for example, water, alcohols, polyols, glycerol, vegetable oils, and the like.

Suitable excipients for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants.

The compounds of formula I as described above can be administered orally or by injection, for the treatment of neoplastic diseases such as leukemia, to warm-blooded animals which need such treatment. More specifically, the compounds of formula I as described above can be administered orally to an adult human in dosages that are in the range of about 0.25 to 50 μg per day for the treatment of neoplastic diseases such as leukemia.

The compounds of formula I as described above can be administered orally, for the treatment of hyperproliferative skin diseases such as psoriasis, basal cell carcinomas, disorders of keratinization, and keratosis, to warm-blooded animals which need such treatment. More specifically, the compounds of formula I as described above can be administered orally to an adult human in dosages that are in the range of about 0.25 to 50 μg per day for the treatment of hyperproliferative skin diseases such as psoriasis, basel cell carcinomas, disorders of keratinization, and keratosis. These compounds can be administered orally for the treatment of acne in humans at a dosage of about 0.25 to 50 μg per day; preferably 0.5 to 5 μg per day.

The compounds of formula I as described above can be administered topically, for the treatment of hyperproliferative skin diseases such as psoriasis, basel cell carcinomas, disorders of keratinization, and keratosis, to warm-blooded animals which need such treatment. More specifically, the compounds of formula I as described above can be administered topically in dosages that are in the range of about 0.5 to 100 μg per gram of topical formulation per day, for the treatment of hyperproliferative skin diseases such as psoriasis, basal cell carcinomas, disorders of keratinization, and keratosis.

The compounds of formula I as described above can also be administered topically for the treatment of sebaceous gland diseases such as acne or seborrheic dermatitis in dosages that are in the range of 0.5 to 100 mg per gram of topical formulation per day.

The useful activity of the compounds of formula I as agents for the treatment of neoplastic diseases can be demonstrated by the following test procedures.

HL-60 Cell Differentiation

The induction of differentiation of HL-60 cells was assayed by measuring their oxidative burst potential via the reduction of NBT (Nitrobluetetrazolium).

HL-60 cells were maintained in RPMI 1640 medium supplemented with 10% FCS, 2 mM L-glutamine, 1 mM sodium pyruvate, 1% non-essential amino acids, 50 U/ml penicillin and 50 μg/ml streptomycin (=RPMI/FCS). 30,000 cells/90 μl of RPMI/FCS were seeded into flat-bottomed microtiter wells. 10 μl of vitamin D derivatives diluted in complete medium were added at the same time to yield final concentrations between $10^{-11}$ and $10^{-6}$M (stock solutions of $10^{-2}$M in ethanol were kept at −20° C. and protected from light). After 3 days, the medium was removed with a multichannel pipette and replaced with 100 μl of NBT solution (1 mg/ml in PBS with 200 mM phorbol myristate acetate (PMA). Following an additional hour incubation at 37° C., the NBT solution was removed and 100 μl of 10% SDS in 0.01N HCl was added. The amount of the reduced NBT was quantified photometrically at 540 nm using an automated plate reader. The mean of 3 wells was calculated. S.E.M. were between 5 and 10%.

Values were expressed as percent of maximal differentiation achieved with 100–1000 nM calcitriol in the same experiment. The concentration (nM) leading to 50% of this maximal value is determined graphically and given as $ED_{50}$ in Table I below.

TABLE I

| COMPOUND | $ED_{50}$(nM) |
| --- | --- |
| 1,25-Dihydroxycholecalciferol (calcitriol) | 8.0 |
| 1,25-(R,S)Dihydroxy-16-ene-23-yne-26-trifluoro-cholecalciferol | 0.15 |
| 1,25(R,S)-Dihydroxy-16-ene-23-yne-26-trifluoro-19-nor-cholecalciferol | 0.37 |
| 1α-Fluoro-25(R,S)-hydroxy-16-ene-23-yne-26-trifluoro-cholecalciferol | 3.70 |
| 25(R,S)-Hydroxy-16-ene-23-yne-26-trifluoro-cholecalciferol | 160.00 |

The useful activity of compounds of formula I as agents for the treatment of hyperproliferative skin disease can be determined by the following.

Inhibition of Keratinocytes Proliferation

HaCaT cell line—The immortalized human cell line HaCaT was used. $^3$H-thymidine incorporation was measured in exponentially growing cultures after 6 days of culture in presence of the test compound.

Cell culture—HaCaT cells were cultured in Dulbecco's Modified Eagle Medium (DMEM) and Nutrient Mixture Ham's F12 (F12), 3:1 (v/v, ICN) containing 4.5 g/l glucose and supplemented with 10% fetal calf serum (Gibco, FCS), L-glutamine (Gibco, 2mM), penicillin (Gibco, 50 UI/ml), streptomycin (Gibco, 50 μg/ml), EGF (10 ng/ml), hydrocortisone (400 ng/ml), cholera toxin (8.5 ng/ml) and insulin (5 ng/ml). The cells were maintained in a humidified atmosphere containing 5% $CO_2$ and 95% air and passaged every 3–4 days.

Inhibition of $^3$H-thymidine uptake—HaCaT cells (250 cells in complete culture medium) were seeded into 96-well culture dishes and incubated at 37° C. with 5% $CO_2$ and 95% air for 6 days. Inhibitors, dissolved at 10× concentration in 1% ethanol, were added immediately at the beginning of the assay. $^3$H-thymidine (5 Ci/mmol, Amersham) was added at a concentration of 1 μCi/well and cells were pulse-labelled for the last 6 hours of the growth period. Cells were then trypsinized for 10 minutes at 37° C. under a vigorous agitation and harvested on to a 96-well GF/C filter plate (Uni Filter, Packard) using a Micro Mate 196 cell harvester (Packard). After drying at 40° C. under vacuum for 20–30 minutes, 2 μl of Micro Scint 0 scintillator (Packard) were added and the radioactivity bound to the filters was counted on a TOP COUNT (Packard).

The results measured as $IC_{50}$ are set forth in Table II below.

TABLE II

| COMPOUND | $IC_{50}$(nM) |
| --- | --- |
| 1,25(R,S)-Dihydroxy-16-ene-23-yne-26-trifluorocholecalciferol | 10.0 |
| 1,25(R,S)-Dihydroxy-16-ene-23-yne-26-trifluoro-19-nor-cholecalciferol | 5.1 |
| 1α-Fluoro-25(R,S)-hydroxy-16-ene-23-yne-26-trifluorocholecalciferol | 11.0 |
| 25(R,S)-Hydroxy-16-ene-23-yne-26-trifluoro-cholecalciferol | 650.00 |

The useful activity of compounds of formula I as agents for the treatment of sebaceous gland diseases can be demonstrated by the following.

Inhibition of Human Sebocyte Proliferation In Vitro

Sebaceous cells were isolated from adult human sebaceous glands by a combination of enzymatic and mechanical methods (Doran et al., Characterization of Human Cells In Vitro, J. Invest. Dermatol. 96:34–8 (1991)). The cells were cultured in Iscove's medium containing 10% fetal calf serum and 4 μg/ml dexamethasone on a layer of growth-arrested 3T3 mouse fibroblasts. Cells were plated in medium without the test compound and then given test compound in fresh medium, containing the test compound, every 48 hours. On the day of harvesting, the cultures were rinsed with 0.03% EDTA in PBS, to remove only the 3T3 fibroblasts, followed by incubation in 0.05% trypsin/0.03% EDTA. The cells were suspended, mixed vigorously to prepare a single cell suspension and counted in a hemocytometer.

Stock solutions of compounds were made up as $10^{-2}$M solutions in degassed 100% ethanol and stored at −20° C. in the dark. During experimental use, the solutions, which have been aliquoted, were brought to room temperature and used by diluting directly into complete medium to appropriate concentration.

The compounds were tested for the inhibition of proliferation of sebaceous cell growth in vitro at $10^{-6}$, $10^{-7}$ and $10^{-8}$M.

The results are summarized in Table III below as the amount of compound necessary to inhibit the proliferation of sebaceous cells by 50% ($ED_{50}$) in nM as compared to a vehicle-treated culture.

TABLE III

| COMPOUND | $ED_{50}$(nM) |
| --- | --- |
| 1,25(R,S)-Dihydroxy-16-ene-23-yne-26-trifluoro-cholecalciferol | 1.0 |

Calcium Liability (tolerance test in mice)

Profound changes in calcium homeostasis strongly affect the weight development of the animals. This parameter was used as a primary test for tolerance.

Mice (25–30 g body weight) received daily subcutaneous administrations of the vitamin D derivative for 4 consecutive days. Body weight was registered just before and at the end of a 5 day treatment period. The "highest tolerated dose" (HTD) is the dose which results in zero weight gain during this treatment period.

The results are set forth in Table IV below.

TABLE IV

| COMPOUND | HTD(μg/kg) |
| --- | --- |
| 1,25(R,S)-Dihydroxy-16-ene-23-yne-26-trifluoro-cholecalciferol | 1.0 |
| 1,25(R,S)-Dihydroxy-16-ene-23-yne-26-trifluoro-19-nor-cholecalciferol | 2.0 |
| 1α-Fluoro-25(R,S)-hydroxy-16-ene-23-yne-26-trifluoro-cholecalciferol | 20.0 |
| 25(R,S)-Hydroxy-16-ene-23-yne-26-trifluoro-cholecalciferol | 600.00 |

The following Examples are provided to further describe the invention and are not intended to limit it in any way.

EXAMPLE 1

[3aS-[3(1S*),3aa,7a,7ab]]-1,1,1-Trifluoro-6-[3a,4,5,6,7,7a-hexahydro--3a-methyl-7-[trimethylsilyl)oxy-1H-inden-3-yl]-2-methyl-3-heptyn-2--ol (epimers)

To the solution of 1.1 g (3.80 mmol) of [3aS,[3(S*),3aa,7a,7ab]]-[[3a,4,5,6,7,7a-hexahydro-3a-methyl-3-(1-methyl-3-butynyl)-1H-inden-7-yl]oxy]-trimethylsilane in 20 ml anhydrous tetrahydrofuran at −78° C. was added with stirring 2.61 ml (4.18 mmol) of 1.6M n-butyllithium. After stirring for one hour, 0.68 ml (7.6 mmol) of 1,1,1-trifluoroacetone was added, and the reaction mixture was stirred for an additional 1 hr at 78° C. The reaction was quenched with saturated brine and warmed up to room temperature. After dilution with water, it was extracted with ethyl acetate. The combined extracts were washed with water, dried over sodium sulfate, and evaporated to dryness. The crude product was purified by FLASH chromatography on silica gel column with hexane-ethyl acetate 20:1, to give 1.47 g (96.5%) of the amorphous title compound.

EXAMPLE 2

[3aS-[3(1S*)3aa,7a,7ab]]3a,4,5,6,7,7a-Hexahydro-3a-methyl-3-(6,6,6-trifluoro-5-hydroxy-1,5-dimethyl-3-hexynyl)-1H-inden-7-ol (epimers)

To a stirred solution of 1.47 g (3.65 mmol) of [3aS,[3(1S*),3aa,7a,7ab]]-1,1,1-trifluoro-6-[3a,4,5,6,7,7a-hexahydro-3a-methyl-7-[(trimethy-lsilyl) oxy]-1H-inden--3-yl]-2-methyl-3-heptyn-2-ol (epimers) in 15 ml of anhydrous tetrahydrofuran at room temperature under argon was added 8 ml (8.0 mmol) of 1M tetrabutyl ammonium fluoride. The reaction mixture was stirred for 1.5 hours, and then quenched by the addition of ice. It was then diluted with water and extracted with ethyl acetate. The combined extracts were washed with 2N potassium bicarbonate, water until neutral pH, and brine, dried over sodium sulfate, and evaporated to dryness. The crude product was purified by FLASH chromatography on a silica gel column with hexane-ethyl acetate 2:1, to give 1.2 g (100%) of crystalline title compound; m.p. 78°–80° C., $[a]_D^{25}$+20.4° (c 0.5, ethanol ("EtOH"); $^1$H-NMR (CDCl$_3$): d 1.07 (s,3H,CH$_3$), 1.09 (d,3H,J+6.5 Hz, CH$_3$), 1.40 (dt, 1H, Jvic=3 and 12.5 Hz, Jgem=12.5 Hz, CH of CH$_2$), 1.58 (s, 3H, CH$_3$), 1.71–1.98 (m, 5H), 2.00 (m, 1H, Jvic=3 and 7 Hz, Jgem=14.5 Hz, CH of CH$_2$), 2.23–2.45 (m, 5H); 4.19 (brs, 1H, CH), 5.40 (brm, 1H, CH); Calcd. for $C_{18}H_{25}F_3O_2$: C 65.49, H 7.63; Found: C 65.59, H 7.77.

EXAMPLE 3

[3aR-[1(R*),3aa,7ab]]-3a,4,5,6,7,7a-Hexahydro-7a-methyl-1-(6,6,6-trifluoro-5-hydroxy-1,5-dimethyl-3-hexynyl)-4H-inden-4-one (epimers)

To a stirred solution of 300 mg (0.91 mmol) of [3aS,[3(1S*), 3aa, 7a,7ab]]-3a,4,5,6,7,7a-Hexahydro-7a-methyl-1-(6,6,6-trifluoro-5-hydroxy]-1,5-dimethyl-3-hexynyl)-1H-inden-7-ol (epimers) in 8 ml of anhydrous methylene chloride was added 1.402 g (3.73 mmol) of pyridimium dichromate and 70 mg pyridinium-p-toluene sulfonate, and the reaction mixture was stirred for 4 hours. 20 ml of ether was added, stirred for 20 min and filtered over Celite. The Celite plug was washed with 3×50 ml of ether. The combined filtrates were washed with 20 ml of ice cold 1N HCl, water, 2N KHCO3 (40 ml) and water and brine. The aqueous layers were extracted with 2×100 ml ether-ethyl acetate (1:1). The organic layers were dried over sodium sulfate and evaporated to dryness. The crude product was purified by FLASH chromatography on silica gel with hexane-ethyl acetate (3:1), to give 272 mg (91.2%) of amorphous title compound.

EXAMPLE 4

[3aR-[1(1R*),3aa,7ab]]-3,3a,5,6,7,7a-Hexahydro-7a-methyl-1-(6,6,6-trifluoro-1,5-dimethyl-5-[(trimethylsilyl)oxy]-3-hexynyl)-4H-inden-4-one (epimers)

To a stirred solution of 272 mg (0.828 mmol) of [3aR-[1(R*),3aa,7ab]]-3,3a,5,6,7,7a-hexahydro-7a-methyl-1-(6,6,6-trifluoro-5-hydroxy-1,5-dimethyl-3-hexynyl)-4H-inden-4-one (epimers) in 6 ml of anhydrous methylene chloride was added 0.79 mg (5.38 mmol) of trimethylsilyl-imidazole under argon. The reaction mixture was stirred at room temperature for 2.5 hours, and then quenched with 7 ml water. After continuous stirring for 30 min, it was extracted with 3×120 ml ethyl acetate. The organic layers were washed five times with a mixture of water and brine, dried over sodium sulfate and evaporated to dryness. The crude product was purified by FLASH chromatography on a silica gel column with hexane-ethylacetate 10:1, to give 314 mg (94.6%) of the title compound.

EXAMPLE 5

1,25(R,S)-Dihydroxy-16-ene-23-yne-26-trifluoro-cholecalciferol

To a stirred solution of 730 mg (1.25 mmol) of [3S-(1Z,3a,5b)]-[2-[3,5-bis[[1,1-dimethylethyl)dimethylsilyl]oxy]-2-methylenecyclo-hexylidene]ethyl]diphenylphosphine oxide in 7 ml of anhydrous tetrahydrofuran at −78° C. was added 0.758 ml (1.21 mmole) of 1.6M n-butyl lithium in hexane dropwise under argon. After stirring for 5 min, to thus formed red solution was added dropwise over a 10 min period a solution of 314 mg (0.784 mmole) of [3aR-[1(1R*), 3aa,7ab]]-3,3a,5,6,7,7a-hexahydro-7a-methyl-1-[6,6,6-trifluoro-1,5-dimethyl-5-[(trimethyl-silyl)oxy]-3-hexynyl]-4H-inden-4-one (epimers) in 5 ml anhydrous tetrahydrofuran. The reaction mixture was stirred at −78° C. for 1.5 hours, and then quenched by addition of 10 ml of a 1:1 mixture of 2N Rochelle salt and 2N potassium bicarbonate. After warm-up to room temperature, an additional 30 ml of Rochelle salt-potassium bicarbonate solution was added and extracted with 3×130 ml ethyl acetate. The organic layers were washed with brine, dried over sodium sulfate and evaporated to dryness. The residue was purified by FLASH chromatography on a silica gel column with hexane-ethyl acetate 40:1, to give 475 mg of the trisilylated title compound.

To the solution of 475 mg (0.621 mmole) of the trisilylated intermediate in 7 ml of anhydrous tetrahydrofuran was added 4 ml (4 mmole) of a 1M tetrabutyl ammonium fluoride in tetrahydrofuran under argon. The reaction mixture was stirred at room temperature for 17 hrs, additional 2 ml of 1M tetrabutyl ammonium fluoride was added and stirred for additional 5 hrs. It was then quenched with 5 ml of water, and after stirring for 20 min tetrahydrofuran was removed by distillation. The residue was extracted with 3×120 ml ethyl acetate. The organic layers were washed with water and brine, dried over sodium sulfate and evaporated to dryness. The crude product was purified by FLASH chromatography on a silica gel column with hexane-ethyl acetate 1:35 to give 270 mg (74.1%) of the title compound as white foam; $[a]_D^{25}$+26° (c 0.2, EtOH); UV (EtOH); lmax: 203 nm (e 17500), 263 (14120); $^1$H-NMR (CDCl$_3$): d 0.72 (s,3H, CH$_3$), 1.13 (d, 3H, J=6.5 Hz, CH$_3$), 1.58 (s, 3H, CH$_3$), 1.92 (ddd, $^1$H, Jvic=3.5 and 8.5 Hz, Jgem=13 Hz, CH of CH$_2$), 2.21 (dd, $^1$H, Jvic=12 Hz, Jgem=14 Hz, CH of CH$_2$), 2.61 (dd, $^1$H, Jvic=3Hz, Jgem=13.5 Hz, CH of CH$_2$), 2.82 (brm, $^1$H, CH of CH$_2$), 4.24 (brm, $^1$H, CH), 4.45 (brm, $^1$H, CH), 5.02, 5.34 (2s, 2H, CH$_2$), 5.39 (brs, $^1$H, CH), 6.11, 6.38 (AB, 2H, J=11.2 Hz, 2CH).

EXAMPLE 6

1,25(R,S)-Dihydroxy-16-ene-23-yne-26-trifluoro-19-nor-cholecalciferol

To a stirred solution of 630 mg (1.1 mmol) of [3R-(3a,5b,Z)-3,5-bis[[1,1-dimethylethyl)dimethylsilyl]oxy]cyclohexylidene]ethyl]diphenylphosphine oxide in 7 ml of anhydrous tetrahydrofuran at −78° C. was added dropwise 0.685 ml (1.1 mmol) of 1.6M n-butyl lithium in hexane under argon. After stirring for 5 min, to the thus formed red solution was added dropwise in the course of 5 min a solution of 232 mg (0.579 mmol) of [3aR-[1(1R*),3aa,7ab]]-3,3a, 5,6,7,7a-hexahydro-7a-methyl-1-[6,6,6-trifluoro-1,5-dimethyl-5-[(trimethylsilyl)oxy]-3-hexynyl]-4H-inden-4-one (epimers) in 2 ml anhydrous tetrahydrofuran. The reaction mixture was stirred at −78° C. for 1.75 hours. It was then quenched by addition of 10 ml of a 1:1 mixture of 2N potassium bicarbonate and 2N Rochelle salt, warmed up to room temperature, and addition of 30 ml of potassium bicarbonate—Rochelle salt mixture, extracted with 3×100 ml ethyl acetate. The combined extracts were washed with brine, dried over sodium sulfate and evaporated to dryness. The crude product was purified by FLASH chromatography on a silica gel column with hexane-ethyl acetate, to give 145 mg of the trisilylated title compound.

To the stirred solution of 145 mg (0.19 mmol) of the trisilylated intermediate in 2.5 ml anhydrous tetrahydrofuran was added under argon 3 ml (3 mmol) of 1M tetrabutyl ammonium fluoride in tetrahydrofuran, and the reaction mixture was stirred at room temperature for 65 hours. It was then quenched with 5 ml water, stirred 15 min., 20 ml of brine was added and extracted with 3×90 ml of ethyl acetate. The combined extracts were washed with a mixture of water and brine, dried over sodium sulfate and evaporated to dryness. The crude product was purified by FLASH chromatography on silica gel to give 89 mg (33.9%) of the title compound as white foam; $[a]_D^{25}$+76° (c 0.2, EtOH); UV (EtOH); lmax: 242–243 nm (e 27,100), 250–251 (31,800), 260 (21,300); $^1$H-NMR: (CDCl$_3$): d 0.72 (s, 3H, CH$_3$), 1.13 (d, 3H, J=6.3 Hz, CH$_3$), 1.59 (s, 3H, CH$_3$), 1.97 (m, 1H), 2.07 (m, 1H, CH of CH$_2$), 2.15–2.55 (m, 8H), 2.72–2.84 (m, 2H, 2 CH of CH$_2$), 4.06 (brm, 1H, CH), 4.13 (brm, 1H, CH), 5.42 (brs, 1H, CH), 5.96, 6.31 (AB, 2H, J=11.1 Hz, CH CH).

EXAMPLE 7

1α-fluoro-25(R,S)-hydroxy-16-ene-23-yne-26-trifluoro-cholecalciferol

To a solution of 536 mg (1.14 mmol) of [3S-(3a,5b,Z)-2-[2-methylene-3-fluoro-5-[[(1,1-dimethylethyl)dimethylsilyl]oxy] cyclohexylidene]ethyl] diphenyl phosphine oxide in 6 ml of anhydrous tetrahydrofuran at −78° C. was added 0.71 ml (1.14 mmol) of 1.6M n-butyl lithium in hexane, dropwise, under argon. After stirring for 5 min, to the red solution was added 282 mg (0.704 mmol) of [3aR-[1(1R*),3aa,7ab]]-3,3a,5,6,7,7a-hexahydro-7a-methyl-1-[6,6,6-trifluoro-1,5-di-methyl-5 [(trimethylsilyl) oxy]-3-hexynyl]-4H-inden-4-one (epimers) in 4.5 ml anhydrous tetrahydrofuran dropwise over 10 min. The reaction mixture was stirred at −78° C. for 2.5 hours. It was then quenched with 10 ml of a 2N Rochelle salt and warmed up to room temperature. It was further diluted with 25 ml of 2N Rochelle salt, and then extracted with 3×100 ml ethyl acetate. The combined organic layers were washed with brine, dried over sodium sulfate and evaporated to dryness. The residue was purified by FLASH chromatography on silica gel with hexane-ethyl acetate 30:1 and then with 1:4. It gave 380 mg of the disilylated title compound.

To a solution of 380 mg (0.582 mmol) of the disilyl intermediate in 4 ml of anhydrous tetrahydrofuran was added under argon 4 ml (4 mmol) of 1M tetrabutyl ammonium fluoride in tetrahydrofuran. The reaction mixture was stirred at room temperature for 17 hours. It was then quenched with 5 ml water, stirred for 15 minutes, 20 ml of brine was added, and extracted with 3×90 ml ethyl acetate. The combined organic layers were washed with water and brine, dried over sodium sulfate and evaporated to dryness. The crude product was first purified by FLASH chromatography on silica gel with hexane-ethyl acetate 2:1 and then by HPLC on a YMC-50 mm×50 cm silica column with hexane-ethyl acetate 3:2 to give 233 mg (70.9%) of the title compound as white foam; $[a]_D^{25}$+22.5° (c 0.2, EtOH); UV (EtOH): lmax: 242–243 nm (e 11,400), 268–269 (11,050); $^1$H-NMR (CDCl$_3$): d 0.71 (s, 3H, CH$_3$), 1.16 (d, 3H, J=6.5Hz, CH$_3$), 1.43–1.58 (m, 2H), 1.60 (s, 3H, CH$_3$), 1.60–1.88 (m, 4H), 2.02 (m, 2H, CH$_2$), 2.14–2.47 (m, 8H), 2.64 (dd, Jvic=3.8 Hz, Jgem=13.5 Hz, CH of CH$_2$), 2.82 (m, 1H, CH of CH$_2$), 4.24 (m, 1H, CH), 5.12 (s, 1H, CH of CH$_2$), 5.15 (ddd, 1H, J=3.9, 6.6 Hz, JHF=49.5 Hz, CH), 5.41 (s, 2H, CH and CH of CH$_2$), 6.12, 6.40 (AB, 2H, J=11.3 Hz, CH CH).

EXAMPLE 8

25(R,S)-Hydroxy-16-ene-23-yne-26-trifluoro-cholecalciferol

To a solution of 520 mg (1.15 mmol) of [5S,Z)-2-[2-[2-methylene-5-[[(1,1-dimethylethyl)dimethylsilyl]oxy] cyclohexylidene]ethyl] diphenyl phosphine oxide in 6 ml of anhydrous tetrahydrofuran at −78° C. was added dropwise under argon 0.715 ml (1.14 mmol) of 1.6M butyl lithium in hexane. After stirring for 5 min, to the red solution thus formed was added dropwise over 10 min 287 mg (0.716 mmol) of [3aR-[1(1R*),3aa,7ab]]-3,3a,5,6,7,7a-hexahydro-7a-methyl-1-[6,6,6-trifluoro-1,5-dimethyl-5-[(trimethylsilyl)oxy]-3-hexynyl]-4H-inden-4-one (epimers) in 4 ml anhydrous tetrahydro-furan. The reaction mixture was then stirred at −78° C. for 2 hours. It was quenched with 10 ml of a 2N Rochelle salt and warmed up to room temperature. The resulting mixture was diluted with 25 ml 2N Rochelle salt and extracted with 3×100 ml ethyl acetate. The combined organic layers were washed with brine, dried over sodium sulfate and evaporated to dryness. The residue was purified by FLASH chromatography on silica gel with hexane-ethyl acetate 30:1, to give 364 mg of disilylated title compound.

To a solution of 364 mg (0.573 mmol) of the disilyl intermediate in 4 ml of anhydrous tetrahydrofuran was added 4 ml (4 mmol) of 1M tetrabutyl ammonium fluoride in tetrahydrofuran under argon. The reaction mixture was stirred at room temperature for 18 hours. It was then quenched with 10 ml water, stirred for 10 min, 20 ml of brine was added and extracted with 3×90 ml ethyl acetate. The organic layers were combined and washed with water and brine, dried over sodium sulfate and evaporated to dryness. The crude product was purified by FLASH chromatography on silica gel with hexane-ethyl acetate 2:1, and then by HPLC on a YMC 50 mm×50 cm silica column with hexane-ethyl acetate 3:2, to give 238 mg (74%) of the title compound as white foam; $[a]_D^{25}$+47° (c 0.2, EtOH); UV (EtOH): lmax 206 nm (e 16,000), 263 (15,500); $^1$H-NMR (CDCl$_3$): d 0.71 (s, 3H, CH$_3$), 1.13 (d, 3H, J=6.4 Hz, CH$_3$), 1.58 (s, 3H, CH$_3$), 1.93 (m, 1H), 2.03 (ddd, 1H, Jvic=3 and 6 Hz, Jgem=14 Hz, CH of CH$_2$), 2.12 –2.52 (m, 9H), 2.58 (dd, 1H, Jvic=3.5 Hz, Jgem=13 Hz, CH of CH$_2$), 2.82 (m, 1H, CH of CH$_2$), 3.96 (brm, 1H, CH), 4.83 (d, 1H, J=1.7 Hz, CH of CH$_2$), 5.06 (s, 1H, CH of CH$_2$), 5.39 (brs, 1H, CH), 6.12, 6.23 (AB, 2H, J=11.3 Hz, CH CH).

EXAMPLE 9

Soft Gelatin Capsule

| Item | Ingredients | mg/Capsule |
| --- | --- | --- |
| 1 | Compound A | 0.0001–1.0 |
| 2 | Butylated Hydroxytoluene (BHT) | 0.016 |
| 3 | Butylated Hydroxyanisole (BHA) | 0.016 |
| 4 | Miglyol 812 q.s. | 160.0 |

Manufacturing Procedure

1. Suspend BHT and BHA in Miglyol 812. Warm to about 50° C., and stir until dissolved.
2. Dissolve Compound A in the solution from Step 1.
3. Fill the solution from Step 2 in soft gelatin capsules.

NOTE: Perform all manufacturing steps under a nitrogen atmosphere and protect from light Compound A represents a compound of the invention.

EXAMPLE 10

Soft Gelatin Capsule

| Item | Ingredients | mg/Capsule |
| --- | --- | --- |
| 1 | Compound A | 0.0001–1.0 |
| 2 | α-Tocopherol | 0.016 |
| 3 | Miglyol 812 q.s. | 160.0 |

Manufacturing Procedure

1. Suspend α-Tocopherol in Miglyol 812. Warm to about 50° C., and stir until dissolved.
2. Dissolve Compound A in the solution from Step 1.
3. Fill the solution from Step 2 in soft gelatin capsules.

NOTE: Perform all manufacturing steps under a nitrogen atmosphere and protect from light

EXAMPLE 11

Topical Cream

| | mg/gm |
|---|---|
| Compound A | 0.0005–0.10 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. to 100 gm |

1. Melt the Cetyl Alcohol, Stearyl Alcohol, Sorbitan Monostearate, Glyceryl Monostearate and Polyoxyethylene Stearate Blend, Polysorbate 60, Mineral Oil and a portion (60%) of Propylene Glycol together in a stainless steel container at 70° C. in a water bath.
2. Dissolve Butylated Hydroxyanisole and Propylparaben in the material from Step 1 and maintain at 70°–72° C. Record the temperature of the melt.
3. Heat the Sorbitol Solution and the water in a suitable container at 70°–75° C.
4. Add the Edetate Disodium and Methylparaben to the solutions in Step 3 and mix until dissolved. Record the temperature of the aqueous phase.
5. Dissolve the appropriate amount of Compound A in another portion (30%) of the Propylene Glycol in a beaker and add this to the material from Step 2 while mixing. Rinse the container with the remaining (10%) of the Propylene Glycol and add this to the mixture from Step 2. Maintain a nitrogen atmosphere above the product during this and subsequent steps.

NOTE: Once Compound A is added, Steps 5 and 6 must be completed in rapid succession.

6. Add the oil phase from Step 2 to the aqueous phase from Step 5 while emulsifying with a high shear mixer. Rinse the oil phase container by withdrawing a portion of the emulsion and add this immediately to the rest of the emulsion.
7. Continue mixing and allowing the product to cool to 50°–55° C. Remove an aliquot for determination of water content and droplet size. Record the result. Add additional water if necessary.
8. Continue mixing with a paddle mixer until the product cools to room temperature. Record the weight of the final product.
9. Transfer the cream to appropriate containers.

NOTE:
1. The manufacturing has to be done in amber light.
2. The final cream should be packaged within 7 days from completion of its manufacture.

We claim:

1. A compound of the formula

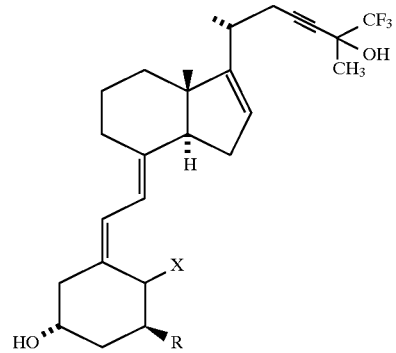

wherein R is hydrogen, fluorine or hydroxy, and X is $=CH_2$ or when R is hydroxy, X is hydrogen or $=CH_2$.

2. The compound of claim 1, wherein R is hydroxy.
3. A mixture comprising epimers of the formula

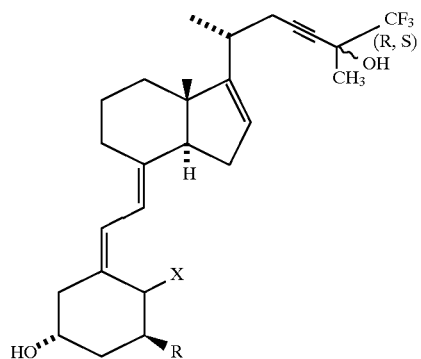

wherein R is hydrogen, fluorine or hydroxy, and X is $=CH_2$ or when R is hydroxy, X is hydrogen or $=CH_2$.

4. 1,25(R,S)-Dihydroxy-16-ene-23-yne-26-trifluoro-cholecalciferol.
5. 1,25(R,S)-Dihydroxy-16-ene-23-yne-26-trifluoro-19-nor-cholecalciferol.
6. 1α-fluoro-25(R,S)-hydroxy-16-ene-23-yne-26-trifluoro-cholecalciferol.
7. 25(R,S)-Hydroxy-16-ene-23-yne-26-trifluoro-cholecalciferol.
8. A pharmaceutical composition comprising an effective amount of the compound of the formula

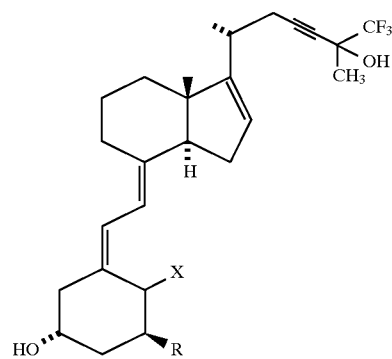

wherein R is hydrogen, fluorine or hydroxy, and X is $=CH_2$ or when R is hydroxy, X is hydrogen or $=CH_2$ and an inert carrier.

* * * * *